US00PP31061P3

(12) United States Plant Patent
Hartman

(10) Patent No.: US PP31,061 P3
(45) Date of Patent: Nov. 12, 2019

(54) ***CALADIUM* PLANT NAMED 'TICKLE ME PINK'**

(50) Latin Name: ***Caladium* X *hortulanum***
Varietal Denomination: Tickle Me Pink

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 15/732,903

(22) Filed: Jan. 13, 2018

(65) Prior Publication Data

US 2019/0223363 P1 Jul. 18, 2019

(51) Int. Cl.
*A01H 5/02* (2018.01)
*A01H 6/00* (2018.01)
*A01H 5/12* (2018.01)

(52) U.S. Cl.
USPC ..... Plt./373
CPC ..... *A01H 6/00* (2018.05); *A01H 5/12* (2013.01)

(58) Field of Classification Search
USPC ..... Plt./373
CPC ..... A01H 6/10; A01H 5/00; A01H 5/02
See application file for complete search history.

(56) References Cited

PUBLICATIONS

Ayne. Color Your World. Apr. 7, 2015. https://aquamarineeyes.wordpress.com/2016/04/12/color-your-world-tickle-me-pink/.*

* cited by examiner

*Primary Examiner* — Keith O. Robinson
(74) *Attorney, Agent, or Firm* — C. A. Whealy

(57) ABSTRACT

A new and distinct cultivar of *Caladium* plant named 'Tickle Me Pink', characterized by its intermediate height and upright and mounding plant habit; vigorous growth habit and rapid growth rate; lance-type leaves that have dark green-colored margins, rose red venation and interveinal areas that are green, tan green and rose red mosaic; petioles that are green or tan pink in color with darker-colored stippling and tessellations; and above average tolerance to wind.

4 Drawing Sheets

Botanical designation: *Caladium* X *hortulanum*.
Cultivar denomination: 'TICKLE ME PINK'.

BACKGROUND OF THE INVENTION

The present invention relates to a new and distinct cultivar of *Caladium* plant, botanically known as *Caladium* X *hortulanum*, commercially referred to as a lance leaf-type *Caladium* and hereinafter referred to by the name 'Tickle Me Pink'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2010 in Avon Park, Fla. of *Caladium* X *hortulanum* 'Florida Sweetheart', disclosed in U.S. Plant Pat. No. 8,526, as the female, or seed, parent with *Caladium* X *hortulanum* 'White Wonder', disclosed in U.S. Plant Pat. No. 21,044, as the male, or pollen, parent. The new *Caladium* plant was discovered and selected by the Inventor as a single plant within the progeny of the stated cross-pollination in a controlled outdoor nursery environment in Zolfo Springs, Fla. in September, 2011.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2012 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Tickle Me Pink'. These characteristics in combination distinguish 'Tickle Me Pink' as a new and distinct *Caladium* plant:

1. Intermediate in height and upright and mounding plant habit.
2. Vigorous growth habit and rapid growth rate.
3. Lance-type leaves that have dark green-colored margins, rose red venation and interveinal areas that are green, tan green and rose red mosaic.
4. Petioles that are green or tan pink in color with darker-colored stippling and tessellations.
5. Above average tolerance to wind.

Plants of the new *Caladium* differ primarily from plants of the female parent, 'Florida Sweetheart', in the following characteristics:

1. Plants of the new *Caladium* are taller than plants of 'Florida Sweetheart'.
2. Plants of the new *Caladium* grow faster and finish about two weeks earlier than plants of 'Florida Sweetheart'.
3. Plants of the new *Caladium* and 'Florida Sweetheart' differ in leaf color as leaves of 'Florida Sweetheart' have dark pink-colored venation, rose pink-colored interveinal areas with greenish white-colored margins.

Plants of the new *Caladium* differ primarily from plants of the male parent, 'White Wonder', in the following characteristics:

1. Plants of the new *Caladium* are taller than plants of 'White Wonder'.
2. Plants of the new *Caladium* and 'White Wonder' differ in leaf color as leaves of 'White Wonder' are white to grey-green in color with light pink to white-colored venation and dark green-colored borders.
3. Plants of the new *Caladium* and 'White Wonder' differ in leaf petiole color as plants of 'White Wonder' have tan green-colored leaf petioles with darker-colored stripes.

Plants of the new *Caladium* can be compared to plants of *Caladium* X *hortulanum* 'Puppy Love', disclosed in U.S. Plant Pat. No. 25,424. In side-by-side comparisons, plants of the new *Caladium* differ primarily from plants of 'Puppy Love' in the following characteristics:

1. Plants of the new *Caladium* grow faster and finish about one week earlier than plants of 'Puppy Love'.
2. Leaves of plants of the new *Caladium* are ovate in shape whereas leaves of plants of 'Puppy Love' are ovate to lanceolate in shape.
3. Plants of the new *Caladium* and 'Puppy Love' differ in leaf color as leaves of 'Puppy Love' are rose red in color with rose red-colored venation and green to whitish green-colored margins.

Plants of the new *Caladium* can be compared to plants of *Caladium* X *hortulanum* 'Blushing Bride', disclosed in U.S. Plant Pat. No. 22,213. In side-by-side comparisons, plants of the new *Caladium* differ primarily from plants of 'Blushing Bride' in the following characteristics:

1. Plants of the new *Caladium* are taller than plants of 'Blushing Bride'.
2. Plants of the new *Caladium* grow faster and finish about one week earlier than plants of 'Blushing Bride'.
3. Plants of the new *Caladium* and 'Blushing Bride' differ in leaf color as leaves of 'Blushing Bride' are greyed purple-colored leaves with dark green-colored margins and whitish-colored venation tinged with greyed purple.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Tickle Me Pink' in a container and grown in a shadehouse (tuber de-eyed).

The photograph at the top of the second sheet is a comparison view of typical potted plants of the female parent, 'Florida Sweetheart' (left), 'Tickle Me Pink' (center) and the male parent, 'White Wonder' (right).

The photograph at the bottom of the second sheet is a comparison view of typical potted plants of 'Puppy Love' (left), 'Tickle Me Pink' (center) and 'Blushing Bride' (right).

The photograph at the top of the third sheet is a comparison view of typical plants of 'Tickle Me Pink' grown in containers; the plant on the left has not had its tuber de-eyed and the plant on the right has had its tuber de-eyed prior to planting.

The photograph at the bottom of the third sheet is a side perspective view of typical plants of 'Tickle Me Pink' grown in an open field.

The photograph at the top of the fourth sheet is a close-up view of typical freshly-harvested tubers with roots and leaf petioles of 'Tickle Me Pink'.

The photograph at the bottom of the fourth sheet is a close-up view of a typical inflorescence of 'Tickle Me Pink'.

DETAILED BOTANICAL DESCRIPTION

The aforementioned photographs and following observations and measurements describe plants grown in 15-cm containers in a polypropylene-covered shadehouse (50% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels were about 10,000 to 12,000 foot-candles. Plants grown in the shadehouse were eight weeks old and plants grown in the outdoor nursery were 7.5 months old when the photographs and the detailed description were taken. In the following description, color references are made to The Royal Horticultural Society Colour Chart, 2001 Edition, except where general terms of ordinary dictionary significance are used.

Botanical classification: *Caladium* X *hortulanum* 'Tickle Me Pink'.

Parentage:

*Female, or seed, parent.*—*Caladium* X *hortulanum* 'Florida Sweetheart', disclosed in U.S. Plant Pat. No. 8,526.

*Male, or pollen, parent.*—*Caladium* X *hortulanum* 'White Wonder', disclosed in U.S. Plant Pat. No. 21,044.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments elliptic to ovate in shape. Height: About 3.8 cm. Diameter: About 5.4 cm to 9.8 cm. Segment height: About 3.1 cm. Segment diameter: About 3.6 cm to 5.4 cm. Axillary buds size: About 4 mm by 4 mm. Texture: Thick, starchy; somewhat brittle. Color:

Epidermis, freshly-harvested: Close to 199B and 158D. Epidermis, dried: Close to 200A. Cortical tissue: Close to 2D. Axillary buds: Close to 36B. Root description: Thick, fleshy contractile roots with few lateral branches; color, close to 155C. Rooting habit: Dense.

Plant description:

*Plant type*.—Herbaceous perennial; suitable as a potted plant in containers 15-cm to 25-cm and suitable as a landscape plant in shaded areas.

*Plant and growth habit*.—Intermediate in height and upright to mounded plant habit; vigorous growth habit and rapid growth rate; potted plants in finished or saleable form in about eight weeks after planting tubers; leaf petioles and leaves arise from one or more growing points on tubers; leaf petioles initially upright and outwardly leaning to arching with development.

*Plant height, from soil level to top of foliar plane, shadehouse-grown potted plants*.—About 24 cm to 31 cm.

*Plant height, from soil level to top of inflorescences, shadehouse-grown potted plants*.—About 27.8 cm.

*Plant diameter or spread, shadehouse-grown potted plants*.—About 33 cm to 39 cm.

*Number of shoots per plant, shadehouse-grown potted plants, tubers not de-eyed*.—About two develop per #1 tuber.

*Number of shoots per plant, shadehouse-grown potted plants, tubers de-eyed*.—About two to three develop per #1 tuber.

*Cataphylls, shadehouse-grown potted plants*.—Length: About 4.5 cm to 8 cm. Width: About 1 cm to 1.2 cm. Shape: Wedge-shaped or lanceolate. Apex: Acuminate to emarginate. Base: Sheathing the stem. Color, inner surface: Close to N155D; colors and patterns on the outer surface are visible on the inner surface. Color, outer surface: Close to N155D tinged with close to 182D and streaked and stippled with close to 147A tinged with close to N200A; with development, color becoming closer to 199B and 200C flushed with close to 187B.

Leaf description:

*Arrangement and type*.—Alternate; simple; lance-type.

*Length, shadehouse-grown potted plants*.—About 19 cm to 30 cm.

*Width, shadehouse-grown potted plants*.—About 12 cm to 16 cm; when flattened, about 12.5 cm to 17.5 cm.

*Shape*.—Ovate.

*Apex*.—Acuminate.

*Base*.—Sagittate to peltate.

*Margin*.—Entire; wavy with broad undulations.

*Texture and luster, upper surface*.—Smooth, glabrous; dull sheen.

*Texture and luster, lower surface*.—Smooth, glabrous; slightly glaucous and dull sheen.

*Venation pattern*.—Pinnate.

*Color, shadehouse-grown potted plants*.—Developing and fully developed leaves, upper surface: Background color: Close to 147A. Margins: Close to 147A; thin leaf edge, close to 187B. Basal notch: Close to 187B. Midvein and primary venation: Close to 53B tinged with close to 185B and close to 53A to 53B surrounded by close to 53C, 53D and 185A. Interveinal areas: Mosaic, close to 147A, 147B, 146A, 159D, 185C and 185D. Developing and fully developed leaves, lower surface: Background color: Close to 191A and close to 191A tinged with close to 189A. Margins: Close to 191A and close to 191A tinged with close to 189A; thin leaf edge, close to 187B. Basal notch: Close to 187C. Midvein: Close to 159D tinged with close to 182D, variably streaked with close to 184D and surrounded by close to 185C and 185D. Primary venation: Close to 159D tinged with close to 194D with occasional flecks, close to 184D and surrounded by close to 185C and 185D. Interveinal areas: Mosaic, close to 147B, 147C, 146B, 184C, 185D and 191B.

*Petioles*.—Aspect: Initially upright and straight and outwardly leaning and arching with development; flexible. Length, shadehouse-grown potted plants: About 15 cm to 23 cm. Diameter, distally, shadehouse-grown potted plants: About 4 mm to 5 mm. Diameter, proximally, shadehouse-grown potted plants: About 6 mm to 9 mm. Texture: Smooth, glabrous. Color, shadehouse-grown potted plants: When developing and fully developed: Close to 199D tinged with close to 181D and 147C stippled, streaked and tessellated with close to 147A. Wing length, shadehouse-grown potted plants: About 4.7 cm to 6 cm. Wing diameter, shadehouse-grown potted plants: About 1 cm. Texture and luster, inner and outer surfaces: Smooth, glabrous; slightly glossy, distally, glaucous. Wing color, shadehouse-grown potted plants: Inner surface: Close to N155D; colors and patterns on the outer surface are visible on the inner surface. Outer surface: Close to 147C and 146C tinged with close to 181D and 147C stippled streaked and tessellated with close to 147A.

Inflorescence description:

*Inflorescences observed on twelve week-old shadehouse-grown potted plants.*

*Inflorescence arrangement*.—Upright hooded spathes surrounding a columnar spadix borne on a tall upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with camphor note.

*Natural flowering season and flower longevity*.—Plants of the new *Caladium* typically flower during the spring in central Florida; flowers develop about twelve weeks after growth commences; inflorescences last about three days before fading; inflorescences persistent.

*Spathe*.—Length, overall: About 12.2 cm. Length, distal open portion: About 8.5 cm. Length, proximal closed portion: About 3.7 cm. Width, distal open portion: About 2.2 cm. Depth, distal open portion: About 2 cm. Width, at constriction: About 1.2 cm. Width, proximal closed portion: About 2.2 cm. Shape, open portion: Narrowly elliptic. Apex: Acuminate. Base: Obtuse. Margin: Entire; smooth. Texture, front and rear surfaces: Smooth, glabrous. Luster, front surface: Dull sheen. Luster, rear surface: Dull sheen, slightly glaucous. Color, front surface: Distal open portion: Close to 157A; with development, color distally becoming closer to 199A. Proximal closed portion: Close to 194C; towards the base, darkly flushed, mottled and streaked with close to N186C and N186D; color does not change with development. Color, rear surface: Distal open portion: Close to 157A and 150D mottled with close to 148C and 148D; color does not change with development. Proximal closed portion: Close to 148C and 147C mottled and flecked with close to 148D; color does not change with development.

*Spadix*.—Length, overall: About 8.2 cm. Length, male flower zone: About 4.7 cm. Length, sterile zone: About 1.5 cm. Length, female flower zone: About 2 cm. Diameter, male flower zone: About 9 mm. Diameter, sterile flower zone: About 6 mm. Diameter, female flower zone: About 1 cm. Shape: Columnar, spindle-shaped. Apex: Acute. Base: Obtuse. Aspect: Upright. Color, mature, male zone: Close to 159C. Color, mature, sterile zone: Close to 159D. Color, mature, female zone: Close to 158C. Male flowers: Quantity per spadix: About 220. Shape: Obovate. Height: About 2 mm. Diameter: About 2.5 mm. Pollen amount: Moderate. Pollen color: Close to 9D. Female flowers: Quantity per spadix: About 200. Shape: Obovate. Height: About 2 mm. Diameter: About 1 mm. Stigma color: Close to 11D. Ovary color: Close to 158C.

*Scape*.—Length: About 15.6 cm. Diameter: About 6 mm. Strength: Sturdy; flexible. Aspect: Mostly erect. Texture and luster: Smooth, glabrous; dull sheen, slightly glaucous. Color: Close to 199D tinged with close to 181D and 147C stippled, streaked and tessellated with close to 147C; distally, close to 147C faintly stippled and streaked with close to 200C to 200D.

*Seeds and fruits*.—To date, seed and fruit development have not been observed on plants of the new *Caladium*.

Pathogen & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'Tickle Me Pink' as illustrated and described.

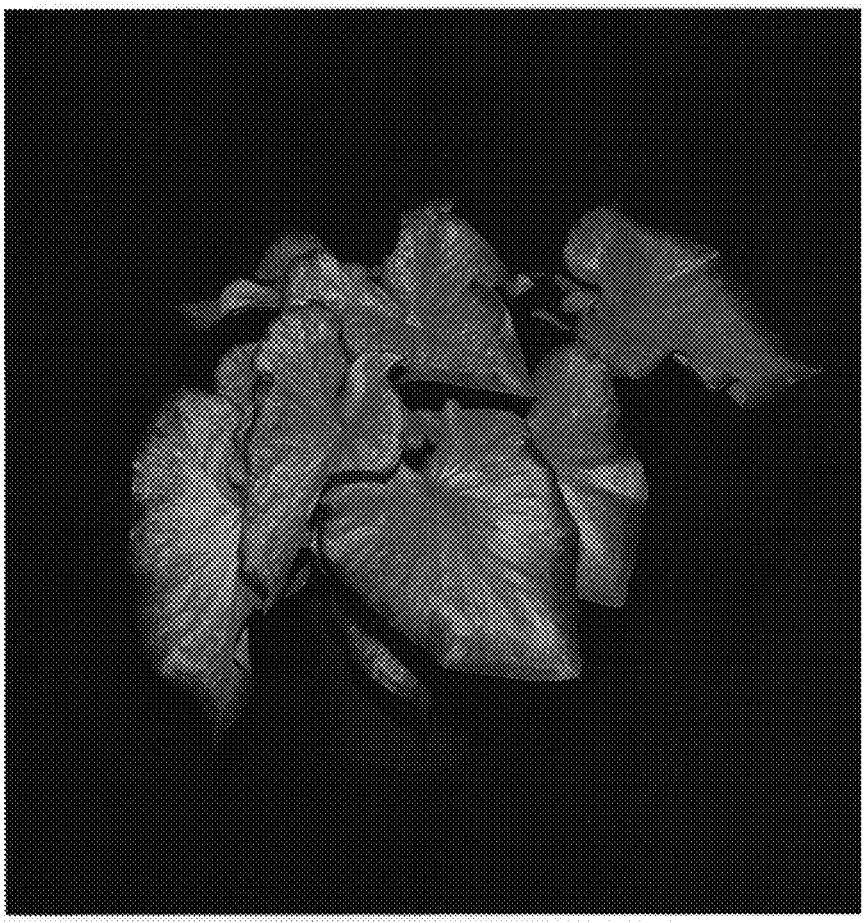

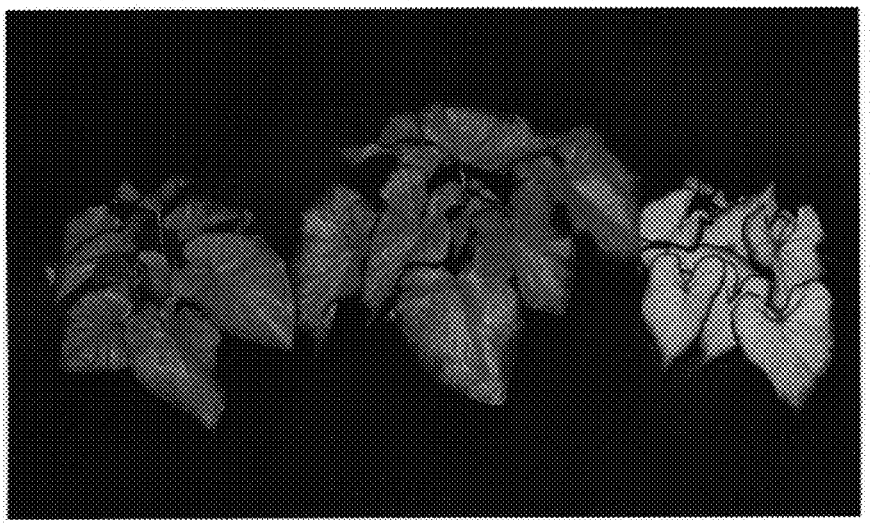
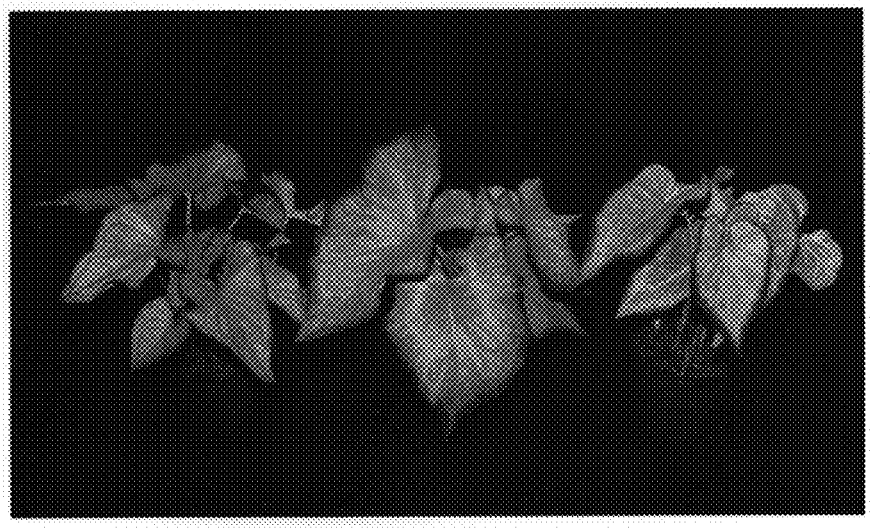

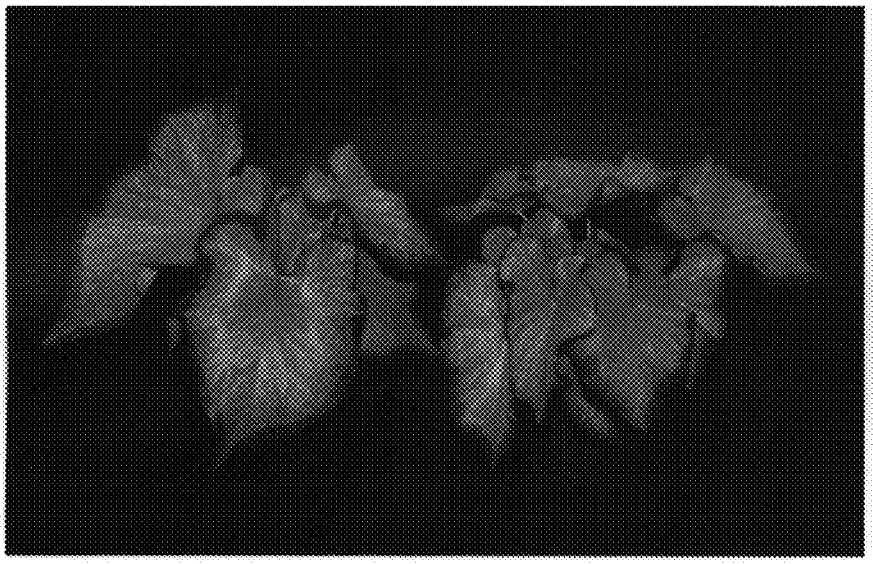
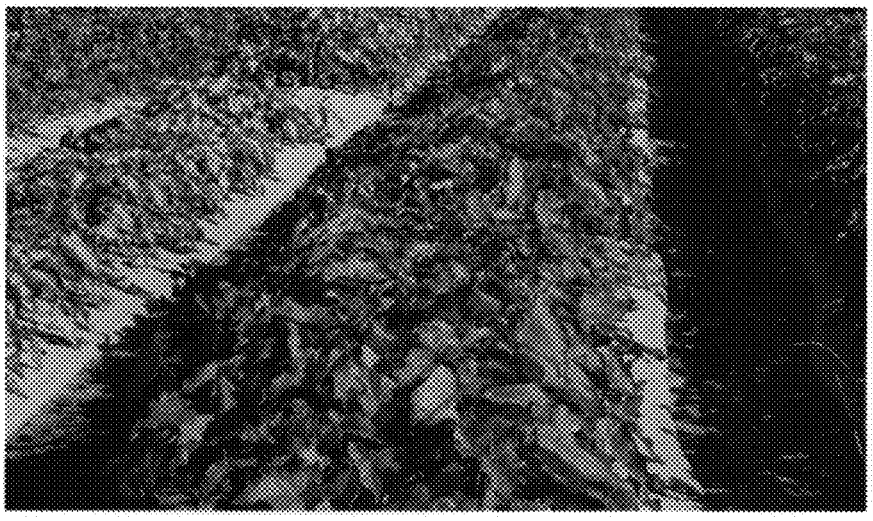

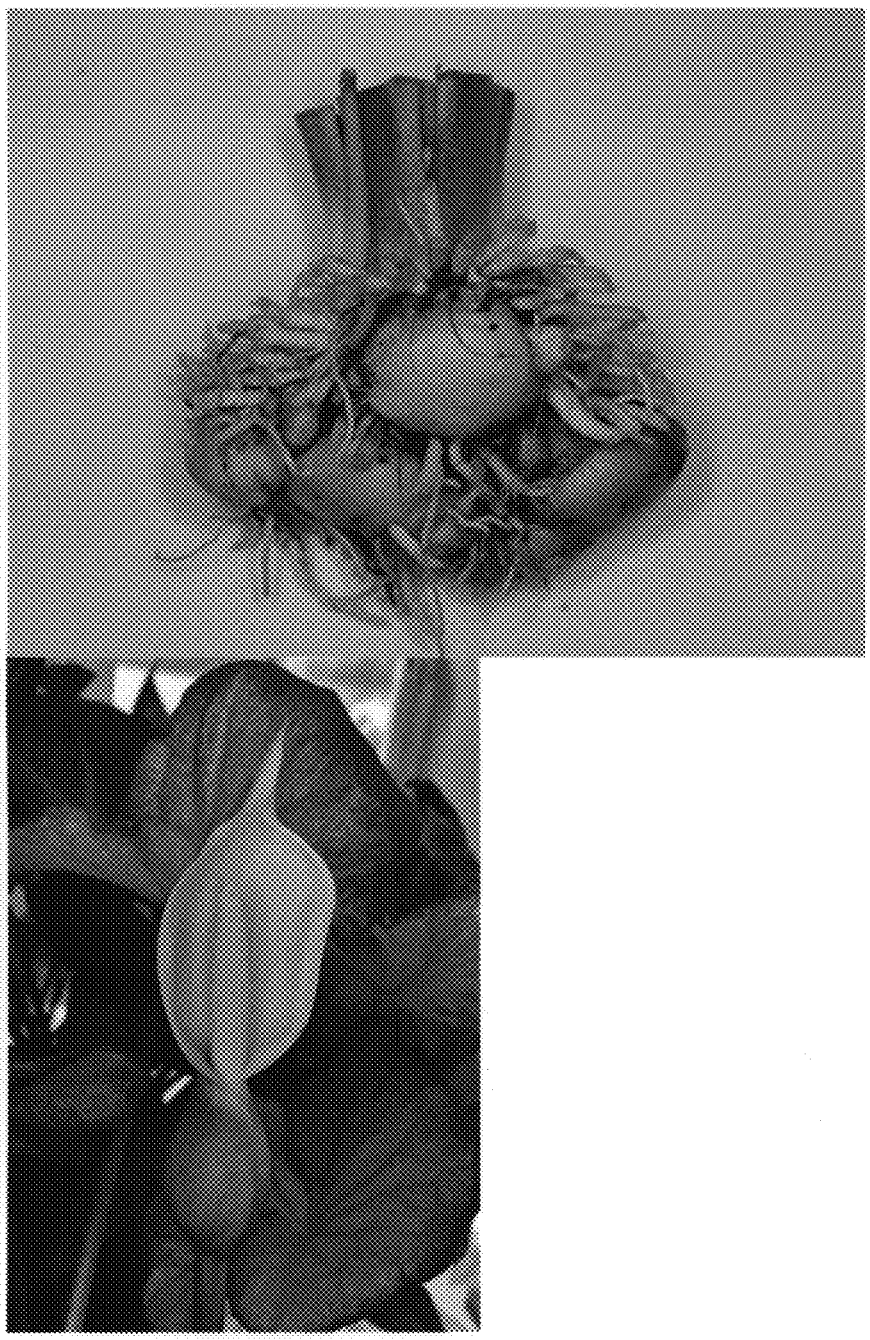

* * * * *